(12) United States Patent
Dioguardi et al.

(10) Patent No.: US 8,503,798 B2
(45) Date of Patent: Aug. 6, 2013

(54) METHOD AND APPARATUS FOR ANALYZING CLUSTERS OF OBJECTS

(75) Inventors: Nicola Dioguardi, Milan (IT); Carlo Russo, Corsico (IT); Fabio Grizzi, Milan (IT); Barbara Franceschini, Pogliano Milanese (IT)

(73) Assignee: Humanitas Mirasole S.p.A., Rozzano (IT)

( * ) Notice: Subject to any disclaimer, the term of this patent is extended or adjusted under 35 U.S.C. 154(b) by 1304 days.

(21) Appl. No.: 12/280,734

(22) PCT Filed: Feb. 28, 2006

(86) PCT No.: PCT/EP2006/060323
§ 371 (c)(1),
(2), (4) Date: Oct. 9, 2008

(87) PCT Pub. No.: WO2007/098803
PCT Pub. Date: Sep. 7, 2007

(65) Prior Publication Data
US 2009/0022388 A1   Jan. 22, 2009

(51) Int. Cl.
*G06K 9/62* (2006.01)

(52) U.S. Cl.
USPC ........................................................ 382/224

(58) Field of Classification Search
USPC .................. 382/181, 224, 228; 707/722, 757
See application file for complete search history.

(56) References Cited

U.S. PATENT DOCUMENTS

| | | | | |
|---|---|---|---|---|
| 5,966,140 A * | 10/1999 | Popovic et al. | ............... | 345/441 |
| 6,917,720 B1 * | 7/2005 | Caesar et al. | ................. | 382/287 |
| 7,149,357 B2 * | 12/2006 | Lee et al. | ...................... | 382/209 |
| 2004/0213452 A1 * | 10/2004 | Seo et al. | ...................... | 382/154 |
| 2006/0217947 A1 * | 9/2006 | Castanon Fernandez | ...... | 703/10 |

FOREIGN PATENT DOCUMENTS

| | | |
|---|---|---|
| WO | WO 03/071468 | 8/2003 |
| WO | WO 2004/081879 A1 * | 9/2004 |

OTHER PUBLICATIONS

N. Dioguardo et al., "Computer-aided morphometry of liver inflammation in needle biopsies," *World Journal of Gastroenterology*, vol. 11, No. 44, Nov. 28, 2005, pp. 6995-7000.

* cited by examiner

*Primary Examiner* — Edward Park
(74) *Attorney, Agent, or Firm* — Dickstein Shapiro LLP

(57) ABSTRACT

The present invention relates to a method and an apparatus for processing and metrically quantifying images of objects containing clusters of points/spots, such as biological specimens comprising cluster of cells, in particular of human or animal origin, or images thereof. In particular, the present invention relates to a method for processing images of irregularly shaped objects in the form of at least one cluster of punctiform or spot-shaped objects, comprising a stage of acquisition of a digital image of said objects, a stage of image elaboration (IMA-EL) for quantizing said digital image to 1 bit and a stage of metrical processing of said 1-bit quantized image, wherein said stage of metrical processing comprises a stage of object's metrical quantification (QUANT) that on its turn comprises: -a stage of triangularization (TRIANG) for transforming the said at least one cluster of punctiform or spot-shaped objects into a grid of triangles wherein the apexes of the triangles correspond to the center of said punctiform or spot-shaped objects; -a stage of parameter calculation (PAR-CLC) for calculating at least one of the following parameters: -external perimeter of the said grid of triangles; -area (AC) of the said grid of triangles; -area (ACINF) of the said punctiform or spot-shaped objects inside the said grid of triangles; -area (APINF) of the isolated punctiform or spot-shaped objects outside the said at least one cluster; -density (DC) of the said punctiform or spot-shaped objects inside the said at least one cluster.

31 Claims, 3 Drawing Sheets

METHOD AND APPARATUS FOR ANALYZING CLUSTERS OF OBJECTS

The present invention relates to a method and an apparatus for processing and metrically quantifying images of objects containing clusters of points/spots, such as biological specimens comprising cluster of cells, in particular of human or animal origin, or images thereof.

Examples of objects or objects' images containing clusters of points/spots may be represented by biological tissues containing groups of cells such as tissues affected by acute or chronic inflammatory lesions, but also topographical images such as images of towns or cities taken by satellite and the like.

Observation and analysis of human, animal or plant tissues is normally performed by means of a microscope. Workstations are known in which a microscope is operatively connected with a camera or video for acquisition of an image and with a computer for visual analysis and elaboration of the acquired image.

On the other hand, when the diagnosis of a pathology requires the observation of a body part or organ, such observation can be direct or through indirect means, such as radiography, Computerised Axial Tomography (CAT), ecography analysis and the like. Again, an image, i.e. a digital image of the observed body part or organ can be acquired and analysed by means of the computer alone or of the computer/camera system.

In any case, several drawbacks are however present in the known apparatuses. The main drawback concerns the way the acquired image is processed by the computer. It is in fact necessary, in some cases, to evaluate physical and geometrical characteristics of the observed body part or of the biological tissue, in order to assess the evolution of the pathology. Difficulties are encountered when the area covered by clusters of points/spots should be evaluated. In such a case, the known devices do not allow a correct quantification of the requested parameters (perimeter, area, etc.) to be made, with the consequence that the outcome of the analysis may be incorrect or even misleading. A particular example is the metrical quantification of the extension of an inflammatory tissue, that is the area covered by the inflammatory cells that can be grouped in clusters and/or distributed randomly in the analysed tissue.

There is therefore a need of improved apparatuses that allow a correct quantification of the morphometric parameters of any item for which such quantification is requested.

The present invention addresses the above and other problems and solve them with a method and an apparatus as depicted in the attached claims.

Further characteristics and the advantages of the method and apparatus for analyzing objects' images according to the present invention will become clear from the following description of a preferred embodiment thereof, given by way of non-limiting example, with reference to the appended drawings, in which.

Figure 1:
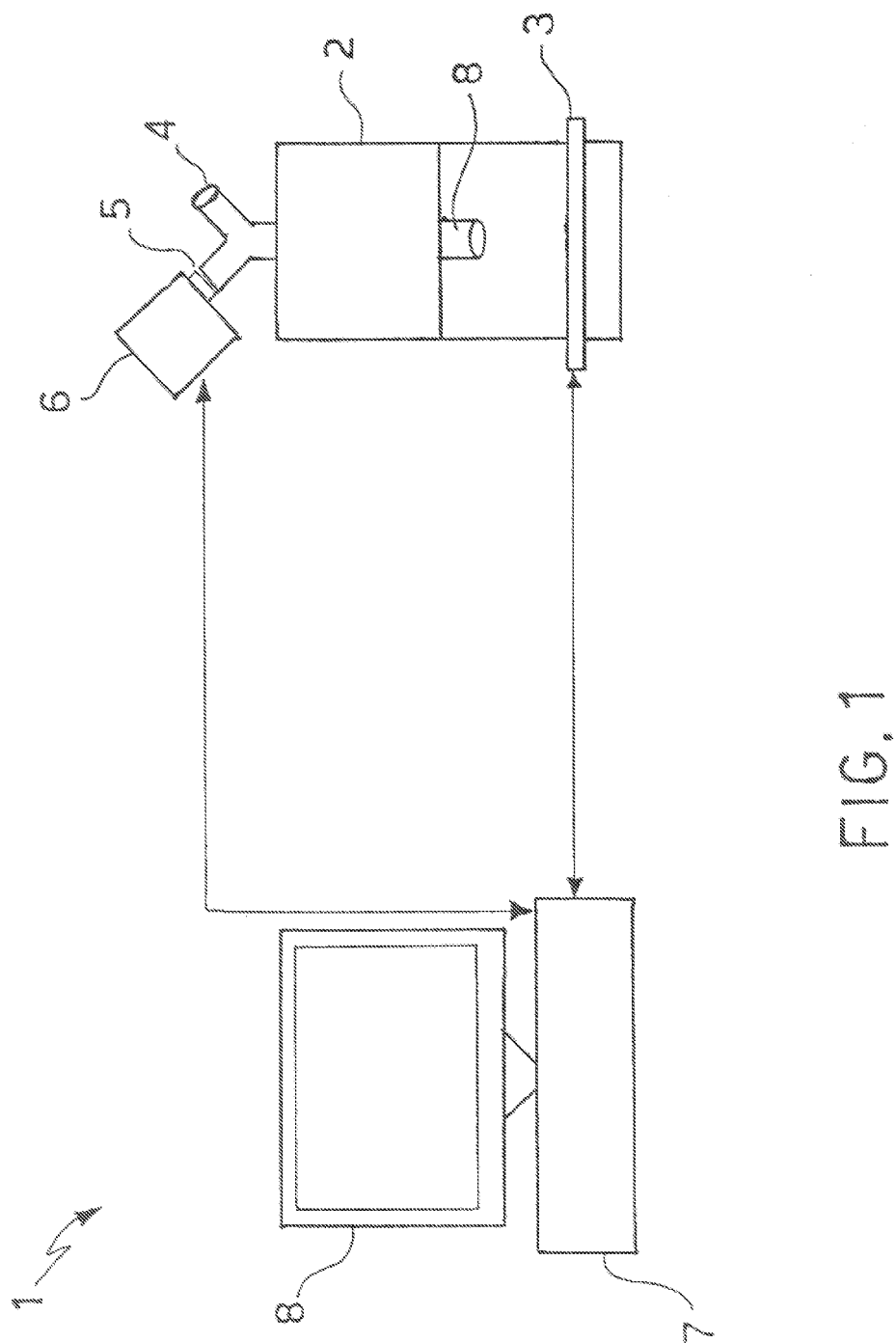
FIG. 1 is a schematic view of the apparatus according to the invention.
Figure 2:
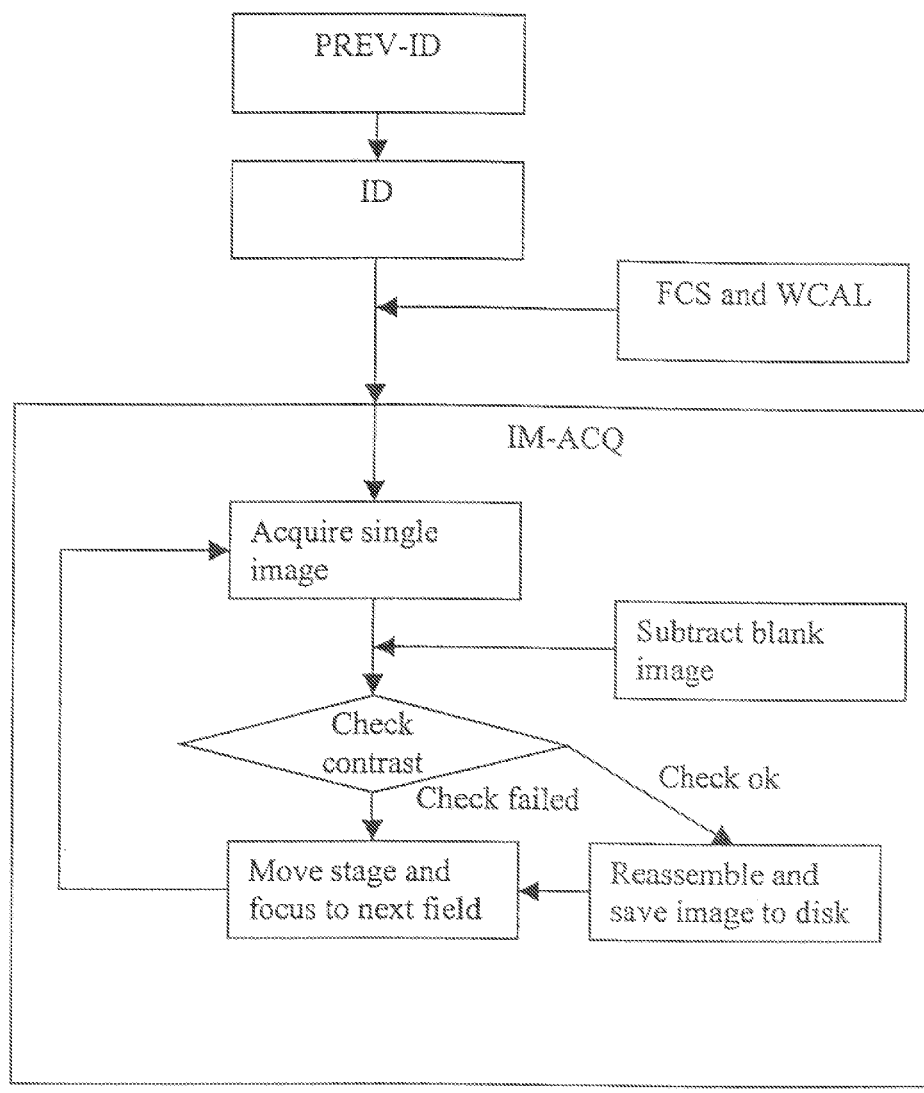
FIG. 2 is a flow chart illustrating the method of acquiring an image according to the invention.
Figure 3:
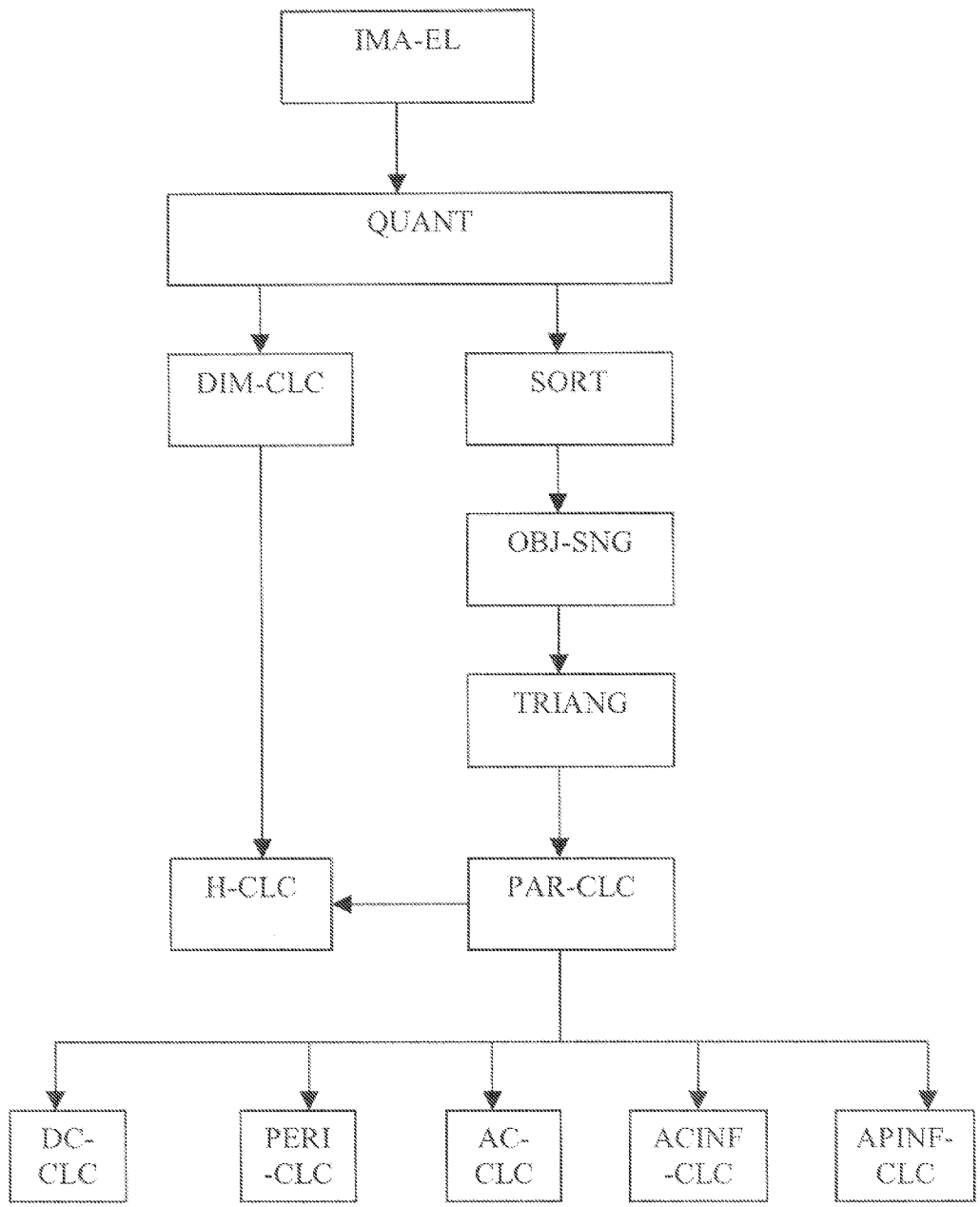
FIG. 3 is a flow chart illustrating the method of processing the acquired image according to the invention.

The method of the invention allows one to analyse and metrically quantify an object's image, particularly the image of an object comprising clusters of points/spots. Such a kind of objects recur often when analysing a biological specimen. However, the method of the invention should not be intended as limited to such a particular application, but can be validly employed in any field of application wherein it is necessary to analyse, whether through microscope observation or by direct image observation, an object's image, such as in the case of a topographical or geophysical survey.

With the term "biological specimens" it is herein intended any kind of biological sample taken from the human, animal or plant body (such as a tissue or cell sample) or any image of a human, animal or plant body part (such as a radiography, ecography, CAT and the like).

The example that will be described hereinafter concerns a system 1 for acquiring and processing an image comprising a microscope 2 having a motorised scanning stage 3 capable of moving along the Cartesian axis x, y, z. The microscope 2 is preferably of the type that allow magnification of from 25× up to 1000×.

The microscope 2 is provided with at least one object glass 8, at least one eyepiece 4 and at least one photo-video port 5 for camera attachment. To this latter, electronic image acquisition means 6, in particular a photo/video camera, are operatively connected. Preferably, such electronic image acquisition means 6 are a digital camera, having more preferably a resolution of 1.3 Megapixels.

The electronic image acquisition means 6 are operatively connected with a processing system 7. The processing system 7 may be realized by means of a personal computer (PC) comprising a bus which interconnects a processing means, for example a central processing unit (CPU), to storing means, including, for example, a RAM working memory, a read-only memory (ROM)—which includes a basic program for starting the computer—, a magnetic hard disk, optionally a drive (DRV) for reading optical disks (CD-ROMs), optionally a drive for reading/writing floppy disks. Moreover, the processing system 7 optionally comprises a MODEM or other network means for controlling communication with a telematics network, a keyboard controller, a mouse controller and a video controller. A keyboard, a mouse and a monitor 8 are connected to the respective controllers. The electronic image acquisition means 6 are connected to the bus by means of an interface port (ITF). The scanning stage 3 is also connected to the bus by means of a control interface port (CITF) by which the movement of the stage along the Cartesian axis is governed.

A program (PRG), which is loaded into the working memory during the execution stage, and a respective data base are stored on the hard disk. Typically, the program (PRG) is distributed on one or more CD-ROMs for the installation on the hard disk.

Similar considerations apply if the processing system 7 has a different structure, for example, if it is constituted by a central unit to which various terminals are connected, or by a telematic computer network (such as Internet, Intranet, VPN), if it has other units (such as a printer), etc. Alternatively, the program is supplied on floppy disk, is pre-loaded onto the hard disk, or is stored on any other substrate which can be read by a computer, is sent to a user's computer by means of the telematics network, is broadcast by radio or, more generally, is supplied in any form which can be loaded directly into the working memory of the user's computer.

Coming now to the description of the method for acquiring and processing an image of a biological specimen according to the invention, the specimen slide is placed on the scanning stage 3 of the microscope 2.

It is pointed out that some of the steps of the method of the invention can be performed by the computer system 7 by executing the program PRG.

The first stage of the method of the invention is the stage of identification of the object whose image should be acquired and quantified (ID stage).

The following method for identifying the object of interest is based on the assumption that such an object is clearly identifiable due to the high contrast of brightness between the object and the background. If such a high contrast is not originally present in the specimen under observation, it can be enhanced for example by staining the specimen with a suitable stain that marks the object or the background.

At the beginning of the ID stage, the magnification is set at the wanted value, in the example 200× magnification. The method starts by:

1a) generating a grid formed by a plurality of boxes to overlap on the image; then,
2a) sending a command by the CPU to the motorized scanning stage 3 to position on the axis x, y in a first position (start position) corresponding to the alignment position of the microscope's object glass with a first box of the grid whose image has to be acquired and a command to the electronic image acquisition means 6 for acquiring the digital image for such a first box, the image being temporarily saved in the RAM memory. Once the image of one box has been acquired,
3a) evaluating by the CPU the brightness of the single pixels in the first box, comparing it with a preset value and determining the brightness contrast inside the box.

The method then goes on by 4a) sending a command to the motorized scanning stage 3 to position on the axis x, y in a next position (second position) corresponding to a second box of the grid, sending a command to the electronic image acquisition means 6 for acquiring and temporarily saving on the RAM memory the digital image for such a second box and repeating the operations of step 3) on such image.

The method is continued by 5a) reiterating the routine of step 4) until the whole slide is scanned and the images for each box of the grid are processed. During the execution of the whole routine, the x, y position of the boxes of the grid having a brightness contrast above a predefined value are saved in the hard-disk memory.

Preferably, step 3a) of processing the image of the box of the grid which has been temporarily saved in the RAM memory is performed according to the following method:

i) building a histogram of the brightness intensities of the pixels of the analysed box,
ii) calculating the standard deviation from the mean value of the histogram, and
iii) comparing the calculated value of standard deviation with a predefined value.

The position of the boxes having a standard deviation above such a predefined value is saved on the hard disk. Such a predefined value of standard deviation will depend upon the kind of object that should be detected, which on its turn depends on the kind of histological tissue, how it is stained, etc.

The procedure described at points i), ii) and iii) is not the only possible for performing step 3), other known methods being suitable, but has the advantage of allowing a reliable result even in the case of a blurred image. It is in fact to be remarked here that, at this stage, focusing of the image has not been usually made yet. Focusing before having identified the object to be observed would result in unacceptable increase of the time spent for the whole procedure.

More preferably, the above ID stage is replaced by or preceded by an identification preview stage (ID-PREV stage) in which the same steps 1) to 5) are performed, but by setting the microscope 2 at a lower magnification (for example, 25× to 100×). This procedure allows a faster execution of the ID stage, since the number of boxes of the grid to iterate will be less. In the case the ID-PREV stage precedes but does not replace the ID stage, this latter will be performed only on the area of the overall image in which the presence of the object has been detected by the ID-PREV.

It should be understood that the object identification stage above described is not strictly necessary for the performance of the method of the invention, even if it allows automatization of the method and a faster execution thereof. In absence of the ID stage and/or ID-PREV stage, identification of the sample can be made manually. On the other hand, absence of an even manual identification stage would cause the further image acquisition stage to be too long, since the whole slide's image would be captured.

The second stage of the method of the invention is the stage of focus setting (FCS stage). According to this second stage:

1b) a plurality of focus points is selected on the object image to be acquired;
2b) the CPU sends a command to the scanning stage 3 to position the first focus point below the microscope's object glass;
3b) said first focus point is brought into focus and its focus parameters are automatically saved in the storing means of the processing system 7;
4b) the routine of steps 2b) and 3b) is repeated for each point.

Step 3b) is preferably performed automatically, by:

3bi) selecting a plurality, preferably five, of focus positions along z drive axis;
3bii) calculating, for each focus position, the brightness contrast, comparing the so obtained brightness contrast values and selecting the focus position with the highest brightness contrast value;
3biii) selecting further two focus positions between the selected focus position and the precedingly and subsequently closer focus positions of step 3bi), respectively;
3biv) reiterating steps 3bi), 3bii) and 3biii) a preset number of times, preferably no more than five times;
3bv) saving the found focus position in the storing means of the processing system 7.

The brightness contrast is obtained according to the procedure described above (step 3a)).

The selected focus points in step 1b) may be equally spaced apart from each other or in any case homogenously distributed on the object's surface. More preferably, nine focus points are selected and are located at the four corners of the largest parallelepiped inscribed into the object under examination, at the center thereof and at the median point of the parallelepiped's sides.

The third stage of the method is the stage of white calibration (WCAL stage). This stage is performed by 1c) acquiring through the electronic image acquisition means 6 the image of a specimen-free region of the slide (blank image) and saving it in the storing means of the processing system 7.

This blank image will be subtracted by the acquired image of each image region in the subsequent image acquisition stage. This will allow to eliminate any borderline shadow effect in the acquired images.

The fourth stage of the method of the invention is the stage of image acquisition (IM-ACQ stage), which is accomplished according to the following steps:

1d) the CPU sends a command to the scanning stage 3 in order to move it to a first saved box position of the grid, selected according to previous step 5a), in alignment with the microscope's object glass;

2d) calculating the focus parameters for said first box image by interpolation from the focus parameters calculated according to previous steps 1b) to 4b) for at least two focus points proximal to the said first box;

3d) acquiring the image of said first box through said image acquisition means 6;

4d) subtracting from the acquired image of said first box the blank image acquired according to step 1c) above;

5d) saving the image resulting from step 4d) in the storing means of the processing system 7;

6d) repeating steps from 1d) to 5d) until the whole object to be acquired has been scanned;

7d) reassembling the whole image of the object by aligning the images of the single boxes in relation to their initial position and saving said whole image in the storing means of the processing system 7.

Preferably, said step 7d) of reassembling the whole image of the object is accomplished by:

l) aligning each box' image with the adjacent box' image by overlapping the edges of the image's side in the direction of alignment;

m) in the region of overlap, minimizing the difference of brightness and/or colour intensity between overlapping pixels by shifting the box' images one with respect to each other;

n) repeating steps l) and m) for each pair of adjacent boxes.

The next stage of the method of the invention is the stage of image elaboration (IMA-EL stage). This stage is performed by quantizing the image to "1 bit" in order to select image's regions on which further calculations are performed. The IMA-EL stage is accomplished according to the following steps:

1e) considering a parameter for each pixel;

2e) comparing said pixel's parameter with a preset threshold value or threshold range for said parameter;

3e) selecting a cluster of active pixels and a cluster of inactive pixels on the basis of said comparison.

Said pixel's parameter is preferably brightness intensity (black and white images) or digital colour value. Said preset threshold value or range for said parameter will depend upon the kind of object that should be detected, which on its turn depends on the kind of histological tissue, how it is stained, etc. or on whether the image is a black-and-white image (such as a radiography) or a coloured image of any kind and origin. Selection of such threshold values or ranges can be made in any case by the skilled man, for the particular case, without exercise of any inventive skill. For example, if the object whose image has to be acquired is an inflammatory cell treated by hymmunohistochemistry, the active pixels may be those having digital values for red between 0 and 255, for blue within 60 and 255 and digital values for green between 0 and 160.

Once the digital image has been quantized to 1 bit, the method of the invention provides for a stage of metrical processing of the image that comprises on its turn different stages that will be depicted herein below.

The next stage of the invention method is thus the stage of object's metrical quantification (QUANT stage).

The first step of the QUANT stage is the calculation of the area of the object under examination. The unit of measurement may be $\mu m^2$ or pixel. The area A of the object under examination is thus calculated by counting the number of pixels belonging to the cluster of active pixels selected according to the previous IMA-EL stage and multiplying the result for the area of a pixel. The area of a pixel is a known parameter that depends on several factors, such as the digital videocamera parameters, the magnification and the like.

In this way, the total area $A_T$ of the clustered and non-clustered (randomly distributed) sets of points/spots is calculated. In the case of a biological tissue containing sets of cells (i.e., inflammatory cells or the like), each point/spot corresponds to a cell or to a cell subset wherein the cells cannot be singled out. The total area of the clustered and non-clustered cells $A_{TINF}$ can be calculated by summing up the area of each point/spot.

Given the considerable irregularity of the perimeter of the cells of the cell subsets under examination and in order to be able to meter their area with good approximation, an evaluation of its fractal dimension $D_A$ is made. This fractal dimension can be automatically determined using the known "box-counting" algorithm.

According to the "box-counting" method, the fractal dimension D is given by the mathematical formula $$D = \lim(\epsilon \to 0)[\log N(\epsilon)/\log(1/\epsilon)]$$

wherein $\epsilon$ is the length of the side of the boxes of the grid in which the object's image has been divided and $N(\epsilon)$ is the number of boxes necessary to completely cover the area $(D_A)$ of the measured object. The length $\epsilon$ is expressed in pixel or $\mu m$ and, in the present calculation method, $\epsilon$ tends to 1 pixel.

The next stage of the invention method is thus the stage of dimensional calculation (DIM-CLC stage).

In order to avoid difficulties in such a calculation, the fractal dimension $D_A$ is approximated as the slope of the straight line obtained by putting in a Cartesian axis system the parameters $\log N(\epsilon)$ versus $\log(1/\epsilon)$.

In practice, the method used to determine $D_A$ comprises the following steps, performed by the CPU of the processing system 7:

a) dividing the image of the object into a plurality of grids of boxes having a side length $\epsilon$, in which $\epsilon$ varies from a first value substantially corresponding to the side of the box in which said object is inscribed and a predefined value which is a fraction of said first value, b) calculating a value of a logarithmic function of $N(\epsilon)$, in which $N(\epsilon)$ is the number of boxes necessary to completely cover the area (A) of the object (cell or cell subset) and of a logarithmic function of $1/\epsilon$ for each $\epsilon$ value of step a), thus obtaining a first set of values for said logarithmic function of $N(\epsilon)$ and a second set of values for said logarithmic function of $1/\epsilon$, c) calculating the fractal dimension $D_A$ as the slope of the straight line interpolating said first set of values versus said second set of values of step b).

As said previously, the calculation of the area $A_T$ or $A_{TINF}$ is made by standard morphometrical evaluation on the active pixels selected according to the IMA-EL stage above described, i.e. by counting the number of active pixels belonging to the same region. To do so, the active pixels belonging to a same region, i.e. to the same small object, must be first of all identified, then each region's area is calculated. Therefore, the method of the invention comprises a stage of object's sorting (SORT stage) which includes the following steps:

1f) scanning of the image quantized to "1 bit" along a predefined direction on a x, y axis system;

2f) selecting a first active pixel along said direction of scanning, said active pixel being identified by a first set of x, y values, said first active pixel belonging to a first object's image;

3f) performing on said first selected active pixel a search routine in the positions next to said selected pixel on the direction's line;

4f) iterating step 3f) until an inactive pixel is found;

5f) assigning to each active pixel selected according to such steps 3f) and 4f) a set of x, y values, saving them in the storing means of the processing system 7 (all of such pixels will have the same y value and x values in progressive order) and switching said pixels from active to inactive in the object's image;

6f) evaluating for each pixel selected according to steps 3f), 4f) and 5f) the two next pixels in the direction orthogonal to the said scanning direction and selecting the active pixels;

7f) performing, for each of said active pixels selected according to step 6f), the routine of steps 3f) to 5f);

8f) iterating steps 6f) and 7f) until all of the connected pixels belonging to the same object have been saved;

9f) repeating steps 1f) and 2f) until a first active pixel of a further object's image is found;

10f) repeating steps 3f) to 9f) until the whole image has been scanned.

Said predefined direction in step 1f) is preferably from left to right starting from top to bottom.

The procedure depicted in steps 1f) to 10f) above allows to identify objects made up from 4-connected pixels, i.e. wherein the pixels have one side in common.

For sorting also 8-connected pixel objects, step 6f) of the above procedure is modified as follows:

6f) evaluating for each pixel selected according to steps 3f), 4f) and 5f) the two next pixels in the direction orthogonal to the said scanning direction and the two pixels adjacent to each of these latter pixels on the parallel line adjacent to the direction's line and selecting the active pixels.

The procedure is then prosecuted according to steps 7f) to 10f).

The procedure depicted above is a semi-recursive method which allows, with respect to the standard recursive methods of the art, shorter execution time and less memory request. In fact, taking into consideration an image made up of N×M active pixels, only M recursive calls are necessary, while according to the prior art methods the number of recursive calls would be N×M−1.

The SORT stage will be completed by the stage of object singularization (OBJ-SNG) according to the following steps:

1g) subdividing objects having at least one of length or width greater than 10 micron into objects of 10 micron side;

2g) calculating the area of the objects identified according to the SORT stage and to step 1g) by counting the number of pixels belonging to said object's image and multiplying it for the area of each pixel;

3g) deleting objects having an area <5 micron$^2$ resulting from step 1g) of subdividing;

4g) overlapping each object identified according to the SORT stage and to steps 1g) to 3g) with a grid of boxes having 10 micron side;

5g) calculating a set of $x_i$, $y_i$ values corresponding to the active pixels of each box of step 4g) and saving it separately in the storing means of the processing system 7, so that each box identifies a single object.

The said step 1g) of subdividing comprises the following steps:

1gi) for each object, finding the polygon circumscribing it having the minimum dimensions nx, my;

1gii) checking whether at least one of nx or my is >10 micron;

1giii) if the check of step 1gii) is positive, overlapping the said polygon with a grid of boxes having 10 micron sides;

1giv) subdividing the said object into portions, each of said portions being inscribed in a box of the grid and disregarding the empty boxes.

After the SORT and OBJ-SNG stages, a stage of triangulation (TRIANG stage) is performed. In the present invention, the triangulation method according to Delaunay's algorithm was used.

Delaunay's triangulation of a cluster of points, in general, provides for a collection of segments connecting each pair of points and satisfying the property of the so called "empty circle". That is to say for each segment it must be possible to find a circle containing only the apexes of that segment, but not other points of the cluster. This algorithm is well known and has been described in several publications: Guibas L. et al, "Primitives for the Manipulation of General Subdivision and the Computation of Voronoi Diagrams", ACT TOG, 4(2), April 1985; Fortune S., "A Sweepline Algorithm for Voronoi Diagrams", Algorithmica, 2:153-174, 1987; Leach G., "Improving Worst-Case Optimal Delaunay Triangulation Algorithms", 4th Canadian Conference on Computational Geometry, 1992.

Therefore, each inflammatory cell on the surface of the histological specimen is considered as a node of a continuous framework covering the entire section made of very irregular triangular sections in which each triangle has a common side with one adjacent triangle. The border of the cluster is arbitrarily identified with the continuous line formed by the most external triangle sides with a length of ≦20 µm, corresponding to about twice the diameter of a lymphocyte (7-12 µm). All the points (cells) circumscribed by this border were considered as belonging to the subset I of cluster-resident cells, while the points connected by longer segments were considered to be non-clustered inflammatory cells (subset II).

Thus, in order to perform the said TRIANG stage, the objects/boxes saved according to step 1gv) above must be transformed into points. Therefore, the TRIANG stage provides for:

1h) calculating the central point of each box saved according to step 5g) having coordinates $x_1+x_2/2$ and $y_1+y_2/2$, wherein $x_1, y_1; x_1, y_2; x_2, y_1; x_2, y_2$ are the coordinates of the apexes of each box, respectively;

2h) saving the x, y values corresponding to each central point of the boxes in the storing means of the processing system 7 as a set of points.

The TRIANG stage then performs the following steps:

3h) considering a couple of points of the set of points obtained according to step 2h);

4h) drawing a circle whose circumference contains the said two points and checking whether the said circle contains other points of the set of points;

5h) drawing a segment between the two points only if the said check is negative and if the distance of said two points is less than or equal to 20 micron;

6h) reiterating steps 3h), 4h) and 5h) on each couple of points of the set of points, thus obtaining a grid of triangles;

7h) saving in the storing means of the processing system 7 a first subset (subset I) of points comprised in the said grid of triangles as cluster-resident points and a second subset (subset II) of points, whose distance from the point that is closest to each is more than 20 micron, as non-clustered points.

The next stage of the method of the invention is the stage of parameters' calculation (PAR-CLC stage).

The first parameter to be calculated is the external perimeter of the grid of triangles obtained by the TRIANG stage (PERI-CLC). This calculation is performed according to the following steps:
1i) indexing each segment of each triangle in the grid of triangles and saving a set of identification indexes for the segments of the grid of triangles;
2i) indexing each segment connecting any borderline point of the cluster-resident points with the closest non-clustered point and saving a set of identification indexes for the non-clustered segments;
3i) summing up the length of segments whose identification index recurs only once in the set of identification indexes of the grid of triangles;
4i) summing up two-fold the length of segments in the set of identification indexes for the non-clustered segments.

The second parameter to be calculated is the area $A_C$ of the cluster (AC-CLC), corresponding to the area of the grid of triangles. This calculation comprises the following steps:
1l) calculating the area of each triangle of the grid of triangles;
2l) summing up the area of all the triangles of the grid of triangles.

The third parameter to be calculated is the area $A_{CINF}$ of the clustered objects (in the specific example, the clustered inflammatory cells) (ACINF-CLC). This calculation is made as described above in the QUANT stage and in step 2g) of the OBJ-SNG stage, i.e. by summing up the active pixels inside the cluster (i.e. inside the perimeter of the grid of triangles) and multiplying the resulting number for the area of each pixel.

The area $A_{PINF}$ of the non-clustered objects (i.e. inflammatory cells) (APINF-CLC) is then obtained by the following expression:

$$A_{PINF} = A_{TINF} - A_{CINF}$$

wherein $A_{TINF}$ is calculated according to the QUANT stage and $A_{CINF}$ is shown just above.

The next parameter to be calculated is the density $D_C$ of the clustered objects (DC-CLC), that is obtained by:

$$D_C = A_{CINF}/A_C$$

The last parameter to be calculated is the Hurst index (H-CLC), according to the following expression:

$$H = E + (1 - D_A)$$

Wherein E is the euclidean dimension (in this case E=1) and $D_A$ is the fractal dimension (see DIM-CLC stage).

It is clear that the above parameters can be used for various purposes. In particular, in the case of the analysis of an inflammatory tissue, these parameters can give useful indications on the status of the disease and the degree of progression of the same.

From what has been said above, it is clear that the calculation method of the invention represents an improvement if compared with the known methods. The fractal geometry offers mathematical models derived from the infinitesimal calculus that, when applied to Euclidean geometry, integrate the figures of the morphometrical measurements of natural and irregular objects, thus making them closer to the actual values.

Even if the above described method is construed for the examination of a tissue specimen by means of a microscope, it is clear that it can also be applied, as said before, to images of the human or animal body or parts thereof, such as for example radiography images, Computerized Axial Tomography (CAT), ecography analysis and the like. In such cases use of the microscope will not be necessary, since the image can be directly digitalised by a videocamera and acquired by the computer software. Substantially the same stages of the method can therefore be applied also for such images, the only difference being the fact that the image acquisition means 6 read the image directly without interposition of a microscope.

In such cases, where identification of small objects or of objects having blurred contour (such as radiographies) is required, the ID stage as described above does not allow an efficient identification, so that different methods should be used.

Possible procedures of object's identification make use of an image representation method called Quad Tree. According to such a known method, the image is firstly divided into four quadrants. Each quadrant is on its turn divided into four sub-quadrants and so on up to reaching quadrants of 1 pixel's side. The image information is reported onto a tree of degree 4, wherein the parent node contains information which is in common with all of the son nodes (from each parent node, four son nodes originate) which refer to the four quadrants into which the parent quadrant is divided.

A first alternative identification procedure suitable for the method of the invention is an image subtraction technics which comprises the following steps:
1m) generating a blurred image of the object to be examined;
2m) subtracting from the image of the object said blurred image in order to obtain an image in which the bright colour regions correspond to the image regions having higher contrast and the dark coloured regions correspond to the image regions having lower contrast;
3m) saving in the storing means of the processing system 7 the image of the regions whose colour or brightness values are above a predefined threshold value.

Preferably, said step 1m) of generating a blurred image is performed by:
dividing the image into quadrants iteratively according to the Quad Tree method up to quadrant having predefined side length (preferably, 1 pixel's side quadrants);
calculating for each quadrant at each division scale the mean value of the pixels, in order to associate to each quadrant a set of values;
generating a colour map (RGB images) or an intensity map (grey scale images) wherein each point value is the mean of the set of values of each quadrant, said colour or intensity map being the blurred image of the original image.

The procedure described herein above is particularly suitable in the case of small objects' detection or to distinguish objects in the foreground from the background.

Furthermore, by modulating the blurring degree, it is possible to discriminate between objects of different dimension, for example by selecting only objects below a predetermined magnitude. In fact, if the Quad Tree procedure is stopped once a minimum quadrant magnitude of for example 10 pixel is reached (instead of a minimum 1 pixel magnitude), the blurring degree is higher, which means that a more blurred image is obtained. If such a more blurred image is subtracted from the object's image according to step 2h) above, all of the objects having a magnitude above 10 pixels are excluded and the resulting image shows just the smaller objects.

A second alternative identification procedure suitable for the ID stage of the method of the invention comprises generating a homogeneity map according to the following steps:

1n) dividing the image into quadrants iteratively according to the Quad Tree method up to quadrant having predefined side length (preferably, 1 pixel's side quadrants);

2n) calculating for each quadrant at each division scale the relative dispersion (RD) obtained as the Standard Deviation divided by the mean value of the pixels, in order to associate to each quadrant a set of values of RD;

3n) generating a homogeneity map as a grey scale image, each point's brightness being given by the mean of the set of values of RD for each quadrant, wherein the image's regions having high brightness correspond to homogeneous regions;

4n) selecting the pixels of the homogeneity map having a brightness intensity above a predefined threshold value and saving their position in the storing means of the processing system 7.

Naturally, only some specific embodiments of the method and apparatus for analyzing biological tissue specimens according to the present invention have been described and a person skilled in the art will be able to apply any modification necessary to adapt it to particular applications without, however, departing from the scope of protection of the present invention.

The invention claimed is:

1. Method for processing images of irregularly shaped objects in the form of at least one cluster of punctiform or spot-shaped objects, comprising a stage of acquisition of a digital image of said objects, a stage of image elaboration (IMA-EL) for quantizing said digital image to 1 bit and a stage of metrical processing of said 1-bit quantized image, wherein said stage of metrical processing comprises a stage of object's metrical quantification (QUANT) that on its turn comprises:

a stage of object singularization (OBJ-SNG) comprising the following steps:

1g) subdividing objects having at least one of length or width greater than 10 micron into objects of 10 micron side;

2g) calculating the area of the objects identified according to the SORT stage and to step 1g) by counting the number of pixels belonging to said object's image and multiplying it for the area of each pixel;

3g) deleting objects having an area <5 micron$^2$ resulting from step 1g) of subdividing;

4g) overlapping each object identified according to the SORT stage and to steps 1g) to 3g) with a grid of boxes having 10 micron side;

5g) calculating a set of $x_i$, $y_i$ values corresponding to the active pixels of each box of step 4g) and saving it separately in the storing means of the processing system (7), so that each box identifies a single object;

a stage of triangularization (TRIANG) for transforming the said at least one cluster of punctiform or spot-shaped objects into a grid of triangles wherein the apexes of the triangles correspond to the centre of said punctiform or spot-shaped objects; and a stage of parameter calculation (PAR-CLC) for calculating at least one of the following parameters:

external perimeter of the said grid of triangles;
area ($A_C$) of the said grid of triangles;
area ($A_{CINF}$) of the said punctiform or spot-shaped objects inside the said grid of triangles;
area ($A_{PINF}$) of the isolated punctiform or spot-shaped objects outside the said at least one cluster;
density ($D_C$) of the said punctiform or spot-shaped objects inside the said at least one cluster.

2. The method of claim 1, further comprising a stage of object's sorting (SORT) for identifying objects made up from 4-connected pixels, which includes the following steps:

1f) scanning of the image quantized to "1 bit" along a predefined direction on a x, y axis system;

2f) selecting a first active pixel along said direction of scanning, said active pixel being identified by a first set of x, y values, said first active pixel belonging to a first object's image;

3f) performing on said first selected active pixel a search routine in the positions next to said selected pixel on the direction's line;

4f) iterating step 3f) until an inactive pixel is found;

5f) assigning to each active pixel selected according to such steps 3f) and 4f) a set of x, y values, saving them in the storing means of the processing system 7 and switching said pixels from active to inactive in the object's image;

6f) evaluating for each pixel selected according to steps 3f), 4f) and 5f) the two next pixels in the direction orthogonal to the said scanning direction and selecting the active pixels;

7f) performing, for each of said active pixels selected according to step 6f), the routine of steps 3f) to 5f);

8f) iterating steps 6f) and 7f) until all of the connected pixels belonging to the same object have been saved;

9f) repeating steps 1f) and 2f) until a first active pixel of a further object's image is found;

10f) repeating steps 3f) to 9f) until the whole image has been scanned.

3. The method of claim 2, wherein said predefined direction in step 1f) is preferably from left to right starting from top to bottom.

4. The method according to claim 2, wherein the stage of object's sorting according to steps 1f) to 10f) of claim 2 is performed for also identifying objects made up from 8-connected pixels, in said stage the step 6f) being modified as follows:

6f) evaluating for each pixel selected according to steps 3f), 4f) and 5l) the two next pixels in the direction orthogonal to the said scanning direction and the two pixels adjacent to each of these latter pixels on the parallel line adjacent to the direction's line and selecting the active pixels.

5. The method of claim 2, wherein the said stage of triangularization (TRIANG) comprises the following steps:

1h) calculating the central point of each box saved according to step 5g) having coordinates $x_1+x_2/2$ and $y_1+y_2/2$, wherein $x_1, y_1; x_1, y_2; x_2, y_1; x_2, y_2$ are the coordinates of the apexes of each box, respectively;

2h) saving the x, y values corresponding to each central point of the boxes in the storing means of the processing system (7) as a set of points;

3h) considering a couple of points of the set of points obtained according to step 2h);

4h) drawing a circle whose circumference contains the said two points and checking whether the said circle contains other points of the set of points;

5h) drawing a segment between the two points only if the said check is negative and if the distance of said two points is less than or equal to 20 micron;

6h) reiterating steps 3h), 4h) and 5h) on each couple of points of the set of points, thus obtaining a grid of triangles;

7h) saving in the storing means of the processing system 7 a first subset (subset I) of points comprised in the said grid of triangles as cluster-resident points and a second subset (subset II) of points, whose distance from the point that is closest to each one is more than 20 micron, as non-clustered points.

6. The method of claim 1, wherein the said step 1g) of subdividing comprises the following steps:
   1gi) for each object, finding the rectangle circumscribing it having the minimum dimensions nx, my;
   1gii) checking whether at least one of nx or my is >10 micron;
   1giii) if the check of step 1gii) is positive, overlapping the said object with a grid of boxes having 10 micron sides;
   1giv) subdividing the said object into portions, each of said portions being inscribed in a box of the grid and disregarding the empty boxes.

7. The method according to claim 1, wherein the said calculation of the external perimeter of the said grid of triangles comprises the following steps:
   1i) indexing each segment of each triangle in the grid of triangles and saving a set of identification indexes for the segments of the grid of triangles;
   2i) indexing each segment connecting any borderline point of the cluster-resident points with the closest non-clustered point and saving a set of identification indexes for the non-clustered segments;
   3i) summing up the length of segments whose identification index recurs only once in the set of identification indexes of the grid of triangles;
   4i) summing up two-fold the length of segments in the set of identification indexes for the non-clustered segments.

8. The method according to claim 1, wherein the calculation of said area ($A_C$) of the grid of triangles comprises:
   1l) calculating the area of each triangle of the grid of triangles;
   2l) summing up the area of all the triangles of the grid of triangles.

9. The method according to claim 1, wherein the calculation of the said area ($A_{CINF}$) of the said punctiform or spot-shaped objects inside the said grid of triangles comprises summing up the active pixels inside the said grid of triangles and multiplying the resulting number for the area of each pixel.

10. The method according to claim 1, wherein the calculation of the said area ($A_{PINF}$) of the isolated punctiform or spot-shaped objects outside the said at least one cluster comprises applying the following expression:

$$A_{PINF} = A_{TINF} - A_{CINF}$$

wherein $A_{TINF}$ is the total area of the objects as calculated by summing up all the active pixels of the image and multiplying the resulting number for the area of each pixel and $A_{CINF}$ is the area of the said punctiform or spot-shaped objects inside the said grid of triangles as calculated.

11. The method according to claim 1, wherein the calculation of the density ($D_C$) of the said punctiform or spot-shaped objects inside the said at least one cluster comprises applying the following expression: $D_C = A_{CINF}/A_C$.

12. The method according to claim 1, further comprising a stage of calculating the Hurst index (H-CLC), according to the following expression:

$$H = E + (1 - D_A)$$

wherein E is the euclidean dimension and $D_A$ is the fractal dimension, wherein the said fractal dimension $D_A$ is calculated in a stage of dimensional calculation (DIM-CLC) comprising:

a) dividing the image of the object into a plurality of grids of boxes having a side length $\epsilon$, in which $\epsilon$ varies from a first value substantially corresponding to the side of the box in which said object is inscribed and a predefined value which is a fraction of said first value, b) calculating a value of a logarithmic function of $N(\epsilon)$, in which $N(\epsilon)$ is the number of boxes necessary to completely cover the area (A) of the object (cell or cell subset) and of a logarithmic function of $1/\epsilon$ for each $\epsilon$ value of step a), thus obtaining a first set of values for said logarithmic function of $N(\epsilon)$ and a second set of values for said logarithmic function of $1/\epsilon$, c) calculating the fractal dimension $D_A$ as the slope of the straight line interpolating said first set of values versus said second set of values of step b).

13. A method according to claim 1, wherein the said stage of image elaboration (IMA-EL) is performed according to the following steps:
   1e) considering a parameter for each pixel;
   2e) comparing said pixel's parameter with a preset threshold value or threshold range for said parameter;
   3e) selecting a cluster of active pixels and a cluster of inactive pixels on the base of said comparison.

14. A method according to claim 13, wherein said pixel's parameter is brightness intensity (black and white images) or digital colour value.

15. A method according to claim 1, wherein said stage of acquisition of the digital image of the object comprises the following:
   stage of providing a system (1) for acquiring and processing an image including a microscope (2) having a motorised scanning stage (3) capable of moving along the Cartesian axis x, y, z, electronic image acquisition means (6) operatively connected to said microscope (2), said motorised scanning stage (3) and said electronic image acquisition means (6) being operatively connected to a processing system (7), said processing system (7) comprising a processing unit (CPU), storing means which include a RAM working memory and a hard disk;
   stage of identification of the object (ID) for saving the cartesian parameters of the object's image, and
   stage of image acquisition (IM-ACQ) of said identified object.

16. A method according to claim 15, wherein said stage of identification of the object (ID) comprises the following steps:
   1a) generating, at a preset magnification of the said microscope (2), a grid formed by a plurality of boxes to overlap on the image;
   2a) sending a command to the motorized scanning stage (3) to position on the axis x, y in a first position (start position) corresponding to the alignment position of the microscope's object glass with a first box of the grid whose image has to be acquired and a command to the electronic image acquisition means (6) for acquiring the digital image for such a first box, the image being temporarily saved in the working memory (RAM);
   3a) evaluating the brightness of the single pixels in the first box, comparing it with a preset value and determining the brightness contrast inside the box;
   4a) sending a command to the motorized scanning stage (3) to position on the axis x, y in a next position (second position) corresponding to a second box of the grid, sending a command to the electronic image acquisition means (6) for acquiring and temporarily saving on the working memory (RAM) the digital image for such a second box and repeating the operations of step 3) on such image;

5a) reiterating the routine of step 4) until the whole slide is scanned and the images for each box of the grid are processed, wherein during the execution of the whole routine, the x, y position of the boxes of the grid having a brightness contrast above a predefined value are saved in the hard-disk memory, wherein said preset magnification of the said microscope (2) is preferably 200× magnification.

17. A method according to claim 16, wherein said step 3a) of processing the image of the box of the grid which has been temporarily saved in the working memory (RAM) is performed according to the following method: i) building a histogram of the brightness intensities of the pixels of the analysed box, ii) calculating the standard deviation from the mean value of the histogram, and iii) comparing the calculated value of standard deviation with a predefined value, wherein the position of the boxes having a standard deviation above such a predefined value is saved on the hard disk.

18. A method according claim 15, further comprising a stage of focus setting (FCS) which includes the following steps:
   1b) a plurality of focus points is selected on the object image to be acquired;
   2b) the CPU sends a command to the scanning stage (3) to position the first focus point below the microscope's object glass;
   3b) said first focus point is brought into focus and its focus parameters are automatically saved in the storing means of the processing system (7);
   4b) the routine of steps 2b) and 3b) is repeated for each point.

19. The method of claim 18, wherein step 3b) is preferably performed automatically, by:
   3bi) selecting a plurality, preferably five, of focus positions along z drive axis;
   3bii) calculating, for each focus position, the brightness contrast, comparing the so obtained brightness contrast values and selecting the focus position with the highest brightness contrast value;
   3biii) selecting further two focus positions between the selected focus position and the precedingly and subsequently closer focus positions of step 3bi), respectively;
   3biv) reiterating steps 3bi), 3bii) and 3biii) a preset number of times, preferably no more than five times;
   3bv) saving the found focus position in the storing means of the processing system (7).

20. The method of claim 18, wherein said selected focus points are equally spaced apart from each other or homogenously distributed on the object's surface.

21. A method according to claim 20, wherein nine focus points are selected and are located at the four corners of the largest parallelepiped inscribed into the object under examination, at the center thereof and at the median point of the parallelepiped's sides.

22. The method according to claim 15, further comprising a stage of white calibration (WCAL), which comprises 1c) acquiring through the electronic image acquisition means (6) the image of a specimen-free region (blank image) and saving it in the storing means of the processing system (7).

23. A method according to claim 15, wherein said stage of image acquisition (IM-ACQ) comprises the following steps:
   1d) sending a command to the scanning stage (3) in order to move it to a first saved box' position of the grid, in alignment with the microscope's object glass;
   2d) calculating the focus parameters for said first box image by interpolation from the focus parameters calculated according to previous steps 1b) to 4b) for at least two focus points proximal to the said first box;
   3d) acquiring the image of said first box through said image acquisition means (6);
   4d) subtracting from the acquired image of said first box the blank image acquired according to step 1c) above;
   5d) saving the image resulting from step 4d) in the storing means of the processing system (7);
   6d) repeating steps from 1d) to 5d) until the whole object to be acquired has been scanned;
   7d) reassembling the whole image of the object by aligning the images of the single boxes in relation to their initial position and saving said whole image in the storing means of the processing system (7).

24. A method according to claim 23, wherein said step 7d) of reassembling the whole image of the object comprises:
   l) aligning each box' image with the adjacent box' image by overlapping the edges of the image's side in the direction of alignment;
   m) in the region of overlap, minimizing the difference of brightness and/or colour intensity between overlapping pixels by shifting the box' images one with respect to each other;
   n) repeating steps l) and m) for each pair of adjacent boxes.

25. A method according to claim 15, wherein said ID stage is performed by:
   1m) generating a blurred image of the object to be examined;
   2m) subtracting from the image of the object said blurred image in order to obtain an image in which the bright colour regions correspond to the image regions having higher contrast and the dark coloured regions correspond to the image regions having lower contrast;
   3m) saving in the storing means of the processing system (7) the image of the regions whose colour or brightness values are above a predefined threshold value.

26. A method according to claim 25, wherein said step 1m) of generating a blurred image comprises:
   dividing the image into quadrants iteratively according to the Quad Tree method up to a quadrant having predefined side length;
   calculating for each quadrant at each division scale the mean value of the pixels, in order to associate to each quadrant a set of values;
   generating a colour map (RGB images) or an intensity map (grey scale images)
   wherein each point value is the mean of the set of values of each quadrant, said colour or intensity map being the blurred image of the original image.

27. A method according to claim 15, wherein said ID stage is performed by:
   1n) dividing the image into quadrants iteratively according to the Quad Tree method up to quadrant having predefined side length;
   2n) calculating for each quadrant at each division scale the relative dispersion (RD) obtained as the Standard Deviation divided by the mean value of the pixels, in order to associate to each quadrant a set of values of RD;
   3n) generating a homogeneity map as a grey scale image, each point's brightness being given by the mean of the set of values of RD for each quadrant, wherein the image's regions having high brightness correspond to homogeneous regions;

4n) selecting the pixels of the homogeneity map having a brightness intensity above a predefined threshold value and saving their position in the storing means of the processing system (7).

28. A method according to claim 15, wherein said system (1) includes a motorised scanning stage (3) capable of moving along the Cartesian axis x, y, z, electronic image acquisition means (6) operatively aligned with said motorised scanning stage (3), said motorised scanning stage (3) and said electronic image acquisition means (6) being operatively connected to a processing system (7), said processing system (7) comprising a processing unit (CPU), storing means which include a RAM working memory and a hard disk.

29. A method according claim 1, wherein said ID stage is replaced by or preceded by an identification preview stage (ID-PREV), which comprises the steps of
- 1a) generating, at a preset magnification of the microscope (2), a grid formed by a plurality of boxes to overlap on the image;
- 2a) sending a command to the motorized scanning stage (3) to position on the axis x, y in a first position (start position) corresponding to the alignment position of the microscope's object glass with a first box of the grid whose image has to be acquired and a command to the electronic image acquisition means (6) for acquiring the digital image for such a first box, the image being temporarily saved in the working memory (RAM);
- 3a) evaluating the brightness of the single pixels in the first box, comparing it with a preset value and determining the brightness contrast inside the box;
- 4a) sending a command to the motorized scanning stage (3) to position on the axis x, y in a next position (second position) corresponding to a second box of the grid, sending a command to the electronic image acquisition means (6) for acquiring and temporarily saving on the working memory (RAM) the digital image for such a second box and repeating the operations of step 3) on such image;
- 5a) reiterating the routine of step 4) until the whole slide is scanned and the images for each box of the grid are processed, wherein during the execution of the whole routine, the x, y position of the boxes of the grid having a brightness contrast above a predefined value are saved in the hard-disk memory, and wherein said preset magnification of the microscope (2) is selected between 25× and 100×.

30. A system (1) for acquiring and processing an image including a motorised scanning stage (3) capable of moving along the Cartesian axis x, y, z, electronic image acquisition means (6) operatively aligned with said motorised scanning stage (3), said motorised scanning stage (3) and said electronic image acquisition means (6) being operatively connected to a processing system (7), said processing system (7) comprising a processing unit (CPU), storing means which include a RAM working memory and a hard disk, said processing system (7) running a program (PRG) to perform a method according to claim 1.

31. A software program (PRG) embodied on a non-transitory computer-readable medium to perform the method according to claim 1.

* * * * *

UNITED STATES PATENT AND TRADEMARK OFFICE
CERTIFICATE OF CORRECTION

PATENT NO.        : 8,503,798 B2                                      Page 1 of 1
APPLICATION NO.   : 12/280734
DATED             : August 6, 2013
INVENTOR(S)       : Dioguardi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1347 days.

Signed and Sealed this

Fifteenth Day of September, 2015

Michelle K. Lee
*Director of the United States Patent and Trademark Office*